United States Patent [19]

Hirono et al.

[11] 4,008,067
[45] Feb. 15, 1977

[54] OXACYCLOHEXANE DERIVATIVES

[75] Inventors: Yoshihiko Hirono, Hiratsuka; Hisao Ishikawa, Odawara; Isao Iwataki, Odawara; Mikio Sawaki, Odawara; Takashi Okabe, Odawara; Daigaku Takiguchi, Tokyo; Kuniyasu Maeda, Yokohama, all of Japan

[73] Assignee: Nippon Soda Company, Limited, Tokyo, Japan

[22] Filed: May 28, 1975

[21] Appl. No.: 581,705

[30] Foreign Application Priority Data

June 4, 1974    Japan .............................. 49-63209

[52] U.S. Cl. ................................ 71/88; 260/340.2; 260/343.5; 260/345.9
[51] Int. Cl.² ................. C07D 319/04; A01N 9/20
[58] Field of Search ................... 71/88; 260/340.2

[56]            References Cited
            UNITED STATES PATENTS

| | | | |
|---|---|---|---|
| 3,737,429 | 6/1973 | Jager et al. | 260/340.2 |
| 3,927,034 | 12/1975 | Sawaki et al. | 260/343.5 |

*Primary Examiner*—Norma S. Milestone
*Attorney, Agent, or Firm*—George B. Oujevolk

[57]            ABSTRACT

A compound of the general formula wherein
$R_1$ is lower alkyl,
$R_2$ is selected from the group consisting of lower alkyl, lower alkenyl and lower alkynyl,
A is a formula which is selected from the formula consisting of:

where
$R_3$ is selected from the group consisting of hydrogen and lower alkyl,
$R_4$ is selected from the group consisting of lower alkyl and phenyl, and
$R_3$ forms cyclo-alkylene of 4 to 5 carbon atoms by combining with $R_4$;

where
$R_5$ and $R_7$ are selected from the group consisting of hydrogen and lower alkyl and
$R_6$ is lower alkyl; and where
$R_8$ is selected from the group consisting of hydrogen and lower alkyl and
$R_9$ is lower alkyl;

or a metal salt of the compound defined herein above is useful as herbicide.

12 Claims, 4 Drawing Figures

OXACYCLOHEXANE DERIVATIVES

DETAILED DESCRIPTION OF THE INVENTION

This invention relates to novel compounds of oxyacyclohexane derivatives, to a process for the preparation thereof and their uses as selective herbicide.

More particularly, this invention is directed to compositions and methods employing, as an active herbicidal ingredient, at least one compound of the general formula:

[I]

wherein
$R_1$ is lower alkyl,
$R_2$ is selected from the group consisting of lower alkyl, lower alkenyl and lower alkynyl,
A is a formula which is selected from the formula consisting of:

(1)  [II]

where
$R_3$ is selected from the group consisting of hydrogen and lower alkyl,
$R_4$ is selected from the group consisting of lower alkyl and phenyl, and
$R_3$ forms cyclo-alkylene of 4 to 5 carbon atoms by combining with $R_4$, (2)  [III]

where
$R_5$ and $R_7$ are selected from the group consisting of hydrogen and lower alkyl and
$R_6$ is lower alkyl; and (3)  [IV]

where
$R_8$ is selected from the group consisting of hydrogen and lower alkyl and $R_9$ is lower alkyl;
or a metal salt of the compound defined herein above.

Preferred for use according to this invention because they are effective as herbicides at lower rates of application are compounds of the formula

[V]

where
$R_1$ is ethyl or propyl;
$R_2$ is ethyl, allyl or propargyl;
$R_3$ and $R_4$ are methyl,

[VI]

where
$R_1$ is ethyl or propyl;
$R_2$ is ethyl, allyl or propargyl;
$R_5$ and $R_7$ are hydrogen;
$R_6$ is ethyl; and

[VII]

where
$R_1$ is ethyl or propyl;
$R_2$ is ethyl, allyl or propargyl;
$R_8$ and $R_9$ are methyl.

Especially preferred for use because of their herbicidal effectiveness are:
2,2-dimethyl-5-[(1-allyloxyamino)propylidene]-1,3-dioxane-4,6-dione,
2,2-dimethyl-5-[(1-allyloxyamino)-n-butylidene]-1,3-dioxane-4,6-dione,
3-(1-ethoxyaminopropylidene)-6-ethyl-tetrahydropyrane-2,4-dione,
3-(1-allyloxyaminopropylidene)-6-ethyl-tetrahydropyrane-2,4-dione,
2,2-dimethyl-3,5-dioxo-4-(1-allyloxyaminopropylidene)tetrahydropyrane.

In addition to the herbicidal effects of the compounds of this invention have both acaricidal and fungicidal activities.

The compounds of this invention can be prepared in accordance with the following equations:

wherein $R_1$, $R_2$, $R_3$, $R_4$, $R_5$, $R_6$, $R_7$, $R_8$ and $R_9$ are as previously defined.

The above reactions can be conducted in an inert solvent.

As an inert solvent, acetone, ether, methylalcohol, ethylalochol, isopropylalcohol, benzene, tetrahydrofuran, chloroform, acetonitrile, dichloroethane, dichloromethane, ethyl acetate, dioxane, toluene, xylene and dimethyl sulfoxide etc. are used.

Reaction temperature is from $-10°$ C to the boiling point of the employed solvent, preferably from 10 to 60 and the reaction terminates between 0.5 and several hours.

After the reaction has terminated, the employed solvent, if necessary, is replaced and then, the reaction mixture is extracted with an alkaline solution and further, an alkaline layer is acidified with hydrochloric acid, whereby the crude product is isolated from the reaction mixture by extraction with a solvent or by filtration.

In case of crystalline substance, the crude product can be purified by recrystallization and in an oily substance the crude product can be purified by distillation or isolation by column chromatography.

The chemical structure for the resulting purified compound can be accurately identified by means of an elementary analysis, NMR spectrum and IR spectrum.

The sodium and potassium salts are prepared by treating a compound of formulae [V], [VI] and [VII] above with a sodium or potassium hydroxide in an aqueous solution or an organic solvent such as acetone, methanol, ethanol or dimethylformamide. The salts are isolated by filtration or by evaporation of the resulting solution.

The calcium, barium, manganese, copper, zinc, nickel, cobalt, iron and silver salts are prepared from the sodium salt by treatment with the appropriate inorganic metal salt, e.q. calcium chloride, barium chloride, copper sulfate, zinc chloride, nickel chloride, and cobalt nitrate.

The starting material [VIII], [IX] and [X] can be prepared in accordance with the following equation:

a)

b)

c)

d)

With respect to the above formulae [V], [VI] and [VII] it is expected that they have the following structural formulae respectively because of tautomerism:

In order that the invention may be better understood, the following examples are given:

EXAMPLE 1.

2,2-dimethyl-5-[(1-allyloxyamino)propylidene]-1,3-dioxane-4,6-dione (Compound No. 4)

To 50 ml of dichloromethane, 22.9 g (0.336 mole) of imidazole was added and further 15.6 g (0.17 mole) of propionyl chloride was added dropwise to it with stirring. After the temperature of the mixture was maintained at 50° C during an hour, 20.2g (0.14 mole) of 2,2-dimethyl-1,3-dioxane-4,6-dione (Meldrum's acid) was added to it and the resulting mixture was allowed to stand for overnight.

After adding 50 ml of water to the reaction mixture and stirring it, the separated water layer was acidified with hydrochloric acid and then was extracted three times with 20 ml of chloroform. The extract chloroform was washed with water and dried over magnesium sulfate, then the solvent chloroform was distilled off under a reduced pressure and thereby the crystallized 4-hydroxy-2,2-dimethyl-5-propionoyl-6H-1,3-dioxin-6-one having a melting point of 55° to 57° C was obtained after drying from the residual material (Yield rate: 48.5%).

NMR spectrum of this compound is as follows: (60 MHz, solvent: $CDCl_3$)

$\delta$: 1.25 ppm 3H (triplet), 1.7 ppm 6H (singlet), 3.1 ppm 2H (quartet), 15.3 ppm H (singlet)

5 g (0.025 mole) of the above 4-hydroxy-2,2-dimethyl-5-propionyl-6H-1,3-dioxin-6-one was dissolved in 10 ml of ethanol and 2.2 g (0.03 mole) of allyloxyamine was added to it, and then the resulting solution was allowed to stand for overnight after warming at 40° C during an hour.

When ethanol was distilled off at a reduced pressure, the residual material crystallized. 5.6 g of crystal having a melting point of 46° to 49° C was obtained after drying at reduced pressure. The desired purified product having a melting point of 48° to 49° C was obtained as colorless plates by recrystallization it from the mixture of n-hexane and toluene (Yield rate: 92.9%).

NMR spectrum of this compound is as follows: (60 MHz, solvent: CDCl$_3$)

δ: 1.25 ppm 3H (triplet), 1.7 ppm 6H (singlet), 3.2 ppm 2H (quartet), 4.5 ppm 2H (doublet), 5.6 ppm 3H (multiplet), 11.8 ppm H (singlet, broad)

EXAMPLE 2

Sodium salt of 2,2-dimethyl-5-[(1-allyloxyamino)propylidene]-1,3-dioxane-4,6-dione (Compound No. 12)

2.5 g of 5-[(1-allyloxyamino)propylidene]-2,2-dimethyl-1,3-dioxane-4,6-dione was dissolved in 1.8 ml of 6 normal sodium hydroxide solution under cooling. Water was distilled off under reduced pressure and 2.8 g of the desired product as colorless powder was obtained after drying.

EXAMPLE 3

2,2-dimethyl-5-[(1-allyloxyamino)-n-butylidene]-1,3-dioxane-4,6-dione (Compound No. 8)

327.4 g (2.27 moles) of 2,2-dimethyl-1,3-dioxane-4,6-dione (Meldrum's acid) was mixed with 179.3 g (2.27 moles) of pyridine and 359.3 g (2.27 moles) of anhydrous butyric acid was added dropwise to said mixture during 50 minutes maintaining the temperature of 10° C, and then, the resulting mixture was allowed to stand for overnight after stirring it during 3 hours at a room temperature.

The reaction mixture was added into the mixture of 300 ml of hydrochloric acid and 300 g of crashed ice with stirring, an oily substance of under layer was separated out and water layer was extracted three times with 200 ml of n-hexane.

The extract n-hexane layer was dried over magnesium sulfate and was decolorized by decoloring charcoal. The solvent n-hexane was distilled off under reduced pressure and thereby 490 g of the oily residual material was obtained. An yield rate was quantitative, but butyric acid of by-product was contaminated. Said butyric acid was distilled off under the pressure of 10 mm Hg and 4-hydroxy-2,2-dimethyl-5-butanoyl-6H-1,3-dioxin-6-one having a refractive index of n$_D^{24}$ 1.4835 was obtained after purification using column chromatography.

NMR spectrum of this compound is as follows: (60 MHz, solvent: CDCl$_3$)

δ: 1.0 ppm 3H (triplet), 1.8 ppm 6H (singlet), 3.1 ppm 2H (triplet), 15 ppm 1H (singlet)

290 g (2.38 moles) of aqueous solution containing 60% allyloxyamine was added to 490 g (2.27 moles) of 4-hydroxy-2,2-dimethyl-5-butanoyl-6H-1,3-dioxin-6-one with stirring and maintaining the temperature of below 40° C during 10 minutes and then the resulting mixture was maintained at the temperature of 40° C during 2 hours.

To the reaction mixture, 400 ml of ethanol was added and the crystal was separated out on standing.

Said crystal was filtrated and washed with a little amount of ethanol and thereby 210 g of the desired 5-[(1-allyloxyamino)-n-butylidene]-2,2-dimethyl-1,3-dioxane-4,6-dione was obtained.

100 g of the same desired product was also obtained by concentrating the above mother liquor. Yield rate: 50.8%, colorless needles, m.p. 82° – 84° C.

NMR spectrum of this compound is as follows: (60 MHz, solvent: CDCl$_3$)

δ: 1.0 ppm 3H (triplet), 1.7 ppm 6H (singlet), 3.1 ppm 2H (triplet), 4.4 ppm 2H (doublet), 5.5 ppm 3H (multiplet)

EXAMPLE 4

Sodium salt of 2,2-dimethyl-5-[(1-allyloxyamino)-n-butylidene]-1,3-dioxane-4,6-dione (Compound No. 14)

0.345 g (0.015 atom) of metallic sodium was dissolved in 8 ml of anhydrous methanol and the resulting methanol solution was added to 20 ml of methanol solution containing 4.05 (0.015 mole) of 5-[(1-allyloxyamino)-n-butylidene]-2,2-dimethyl-1,3-dioxane-4,6-dione.

Methanol was distilled off under reduced pressure at a room temperature and the desired sodium salt was quantitatively obtained as colorless powder after drying under reduced pressure.

EXAMPLE 5

3-(1-ethoxyaminoethylidene)-5,6-dimethyltetrahydropyrane-2,4-dione (Compound No. 21)

0.36 g (0.002 mole) of 3-acetyl-4-hydroxy-5,6-dimethyl-2H-pyrane-2,4-dione was dissolved in 5 ml of ethanol and it was allowed to react with 0.12 g (0.002 mole) of ethoxyamine for an hour at room temperature, further for an additional hour under reflux. Then, said ethanol was distilled off and the resulting oily substance was dissolved in ether. The resulting ether solution was extracted for two times with 2.5 ml of aqueous solution containing 5 weight percent of sodium hydroxide and an alkaline layer produced thereto was acidified with hydrochloric acid, and then the resulting hydrochloric acid solution was extracted for three times with 10 ml of ether.

An ether layer produced thereto was washed with water and was dried with magnesium sulfate, and then it was distilled off under a reduced pressure and thereby, the desired compound, as a colorless and oily substance was obtained.

A yield amount: 0.42 g (93 weight % of yield rate)
A refractive index: n$_D^{24.5}$ 1.5125

EXAMPLE 6

3-(1-allyloxyaminopropylidene)-6-ethyl-tetrahydropyrane-2,4-dione (Compound No. 20)

3.5 g of 6-ethyl-4-hydroxy-3-propionyl-5,6-dihydro-2H-pyrane-2,4-dione was dissolved in 30 ml of ethanol and 2 g of allyloxyamine was added to it, and after the resulting solution was stirred at a room temperature during 2 hours, the said ethanol was distilled off from it under a reduced pressure and an oily substance was dissolved in an aqueous solution containing 5 weight % of sodium hydroxide.

The resulting alkaline solution was extracted with chloroform and an oily substance was obtained by neutralization with hydrochloric acid and separation, and then said oily substance was extracted with ether, and after an ether layer was dried with magnesium sulfate, said ether was distilled off under a reduced pressure and thereby, 4.2 g of the desired compound was obtained. A refractive index: $n_D^{17}$ 1.5191

EXAMPLE 7

2,2-dimethyl-3,5-dioxo-4-(1-allyloxyamino-propylidene)tetrahydropyrane (Compound No. 25)

5.3 g of 2,2-dimethyl-3,4-dioxo-4-propionyl-tetrahydropyrane was dissolved in 50 ml of ethanol and 3.5 g of allyloxyamine was added to it, and after the resulting solution was stirred at a room temperature during 2 hours, said ethanol was distilled off and an oily substance was dissolved in an aqueous solution containing 5 weight % of sodium hydroxide.

The resulting alkaline solution was extracted with chloroform and an oily substance was separated out by neutralizing said chloroform solution with hydrochloric acid. Then, said oily substance was extracted with ether, and after an ether layer was dried with magnesium sulfate, said ether was distilled off and thereby, 6.0 g of the desired compound was obtained. A refractive index: $n_D^{20}$ 1.5187.

In addition to the above mentioned compounds described in the preceding example, some typical compounds of the present invention are listed in Table 1.

Table 1

| Compound No. | Structural Formula | Chemical Name | Physical Constant |
|---|---|---|---|
| 1 | (structure) | 2,2-dimethyl-5-(1-ethoxyaminoethylidene)-1,3-dioxane-4,6-dione | m.p. 91 – 92° C |
| 2 | (structure) | 2,2-dimethyl-5-(1-allyloxyaminoethylidene)-1,3-dioxane-4,6-dione | m.p. 84 – 85° C |
| 3 | (structure) | 2,2-dimethyl-5-(1-ethoxyaminopropylidene)-1,3-dioxane-4,6-dione | m.p. 86.5 – 88.5° C |
| 4 | (structure) | 2,2-dimethyl-5-(1-allyloxyaminopropylidene)-1,3-dioxane-4,6-dione | m.p. 48 – 49° C |
| 5 | (structure) | 2-ethyl-2-methyl-5-(1-ethoxyaminopropylidene)-1,3-dioxane-4,6-dione | $n_D^{25}$ 1.5090 |
| 6 | (structure) | 2-phenyl-5-(1-ethoxy-aminopropylidene)-1,3-dioxane-4,6-dione | m.p. 119 – 120° C |

Table 1-continued

| Compound No. | Structural Formula | Chemical Name | Physical Constant |
|---|---|---|---|
| 7 | (dioxane structure with NHOC₂H₅, C-C₃H₇) | 2,2-dimethyl-5-(1-ethoxyaminobutylidene)-1,3-dioxane-4,6-dione | m.p. 79 – 80° C |
| 8 | (dioxane structure with NHOCH₂CH=CH₂, C-C₃H₇) | 2,2-dimethyl-5-(1-allyloxyaminobutylidene)-1,3-dioxane-4,6-dione | m.p. 83 – 85° C |
| 9 | (dioxane structure with NHOCH₂C≡CH, C-CH₃) | 2,2-dimethyl-5-(1-propargyloxyamino-ethylidene)-1,3-dioxane-4,6-dione | m.p. 114 – 116° C |
| 10 | (dioxane structure with NHOCH₂C≡CH, C-C₂H₅) | 2,2-dimethyl-5-(1-propargyloxyamino-propylidene)-1,3-dioxane-4,6-dione | m.p. 98 – 99° C |
| 11 | Na salt of (dioxane structure with NHOCH₂CH=CH₂, C-CH₃) | Sodium salt of 2,2-dimethyl-5-(1-allyloxyaminoethylidene)-1,3-dioxane-4,6-dione | |
| 12 | Na salt of (dioxane structure with NHOCH₂CH₃, C-C₂H₅) | Sodium salt of 2,2-dimethyl-5-(1-ethoxyaminopropylidene)-1,3-dioxane-4,6-dione | |
| 13 | Na salt of (dioxane structure with NHOCH₂CH=CH₂, C-C₂H₅) | Sodium salt of 2,2-dimethyl-5-(1-allyloxyaminopropylidene)-1,3-dioxane-4,6-dione | |
| 14 | Na salt of (dioxane structure with NHOCH₂CH=CH₂, C-C₃H₇) | Sodium salt of 2,2-dimethyl-5-(1-allyloxyaminobutylidene)-1,3-dioxane-4,6-dione | |

Table 1-continued

| Compound No. | Structural Formula | Chemical Name | Physical Constant |
|---|---|---|---|
| 15 | | 9-(1-allyloxyamino-propylidene)-7,11-dioxaspiro[5,5]undecene-8,10-dione | m.p. 80 – 81.5° C |
| 16 | | 8-(1-allyloxyamino-propylidene)-6,10-dioxaspiro[4,5]-decene-7,9-dione | m.p. 70 – 72° C |
| 17 | | 9-(1-allyloxyamino-butylidene)-7,11-dioxaspiro[5,5]-undecene-8,10-dione | m.p. 96 – 98° C |
| 18 | | 8-(1-allyloxyamino-butylidene)-6,10-dioxaspiro[4,5]-decene-7,9-dione | m.p. 73 – 74° C |
| 19 | | 3-(1-ethoxyamino-propylidene)-6-ethyl-tetrahydropyrane-2,4-dione | $n_D^{17}$ 1.5047 |
| 20 | | 3-(1-allyloxyamino-propylidene)-6-ethyl-tetrahydropyrane-2,4-dione | $n_D^{17}$ 1.5191 |
| 21 | | 3-(1-ethoxyamino-ethylidene)-5,6-dimethyl-tetrahydropyrane-2,4-dione | $n_D^{24.5}$ 1.5125 |
| 22 | | 3-(1-ethoxyamino-ethylidene)-5,5-dimethyl-tetrahydropyrane-2,4-dione | $n_D^{24.5}$ 1.5050 |
| 23 | | 3-(1-ethoxyamino-butylidene)-6-ethyl-tetrahydropyrane-2,4-dione | $n_D^{19}$ 1.5047 |

Table 1-continued

| Compound No. | Structural Formula | Chemical Name | Physical Constant |
|---|---|---|---|
| 24 | Na salt of [structure with NHOC$_2$H$_5$, C—C$_3$H$_7$, CH$_3$, CH$_3$, O] | Sodium salt of 3-(1-ethoxyamino-butylidene)-6,6-dimethyl-tetrahydropyrane-2,4-dione | m.p. 160° C (decomposition) |
| 25 | [structure with NH—O—CH$_2$—CH=CH$_2$, C—C$_2$H$_5$, CH$_3$, CH$_3$] | 2,2-dimethyl-3,5-dioxo-4-(1-allyloxyamino-propylidene)tetrahydropyrane | $n_D^{20}$ 1.5187 |
| 26 | [structure with NH—O—C$_2$H$_5$, C—C$_2$H$_5$, C$_2$H$_5$] | 2-ethyl-3,5-dioxo-4-(1-ethoxyaminopropylidene)tetrahydropyrane | $n_D^{25}$ 1.5095 |
| 27 | [structure with NHOC$_2$H$_5$, C—C$_2$H$_5$, CH$_3$] | 2-methyl-3,5-dioxo-4-(1-ethoxyaminopropylidene)tetrahydropyrane | $n_D^{26}$ 1.5103 |
| 28 | [structure with NHOCH$_2$CH=CH$_2$, C—C$_2$H$_5$, CH$_3$] | 2-methyl-3,5-dioxo-4-(1-allyloxyamino-propylidene)tetrahydropyrane | $n_D^{26}$ 1.5138 |

Hereinafter, the compounds of this invention are represented by Compound No. Table 1.

As mentioned previously, it has been found that the compounds of the invention possess superior herbicidal activity. The paragraphs which follow described in more detail the utility of this invention.

The compounds of the invention are particularly effective in the control of grass weeds such as annual bluegrass (*Poa annua* L.), water foxtail (*Alopecurus aequalis* Sobol), large crabgrass (*Digitaria adscendens* Henr.), green foxtail (*Seturia viridis* Beauv), wild oat (*Avena fatua* L) etc. and they hardly injure broad leaf crops such as adzuki bean (*Phaseolus angularis* W. F. Wight) and soy bean (*Glycine max* Merrill) and sugar beets (*Beta vulgaris* L.) which easily suffer phyto-toxicity. Namely, the compound of the invention are the selective herbicide.

It is already known that 3,4-dihydro-2H-pyrane-2,4-dione derivatives have herbicidal properties as shown in German Patent Publication No. 2,352,661.

However, the compounds of the present invention are superior to said prior art compound for selective weed control in foliar treatment.

In case of foliar treatment using the compounds of the present invention, even the same amount of chemical which kills completely barnyard grass of grass weeds gives no damages to broadleaf plants such as radish (*Raphanus sativus* L.), soy bean, garden pea (*Pisum sativum* L.), spinach (*Spinacia oleracea* L.) sugar beets and carrot (*Daucus carot* L.) at all, and in case of soil treatment before germination, even the same amount of chemicals which prevents large-crab grass germinating gives no damages to seeds of broad leaf plants at al.

As mentioned above, a security to the broadleaf crop against phytotoxicity of the herbicide is extremely high and as to its application, in the other words, its applicable time, its applying location and its applying concentration, it has a very broad extent and it can be used in the wider extent.

It is another advantage of the present invention that a residual toxicity in the soil or the plant and an acute toxicity for worm blooded animals and fish are not feated because the said compounds can be used with a low chemical concentration.

The compounds of this invention can be applied directly to the soil as pre-emergence treatment or to plant foliage, as post-emergence treatment, or they can be mixed intimately with the soil, preferably post-emergence treatment to plant foliage, and may be applied to soil or plant foliar at rates of 50 - 200 g per 10 are, more preferably about 100 g per 10 are.

The method of the present invention comprehends the employment of a liquid or solid composition containing one or more of the present componds as an active ingredient.

The active ingredient of this invention may be formulated by mixing with suitable carriers in a form generally used in agricultural chemicals such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, benzene, xylene, cyclohexane, cyclohexanone, dimethylformamide, alcohol, acetone, water and others are used. Sometimes surface active agent is added in order to give a homogeneous and stable formulation.

The componds of this invention also can be applied admixed with other chemicals which are used in agronomic and horticultural management and are compatible with the compounds of this invention. Such chemicals can be, but are not restricted to, the classes of chemicals commonly known as plant nutrients, fertilizers, insecticides, acaricides, fungicides, herbicides and nematocides.

As for known herbicides it is recommended that the compound of the present invention is applied admixed with the herbicidal compound selected from the group consisting of N-(3-chloro-4-methoxyphenyl)-N',N'-dimethylurea,
N-(3,4-dichlorophenyl)-N',N'-dimethylurea,
N-(3,4-dichlorophenyl)-N'-methoxy-N'-methylurea,
1,3-dimethyl-(3-benzothiazole-2-yl)urea,
1,3-dimethyl-3-(5-methylbenzothiazole-2-yl)urea,
1,3-dimethyl-3-(5-t-butylbenzothiazole-2-yl)urea,
1,1,3-trimethyl-3-(5-methylbenzothiazole-2-yl)urea,
1,1,3-trimethyl-3-(5-ethylbenzothiazole-2-yl)urea,
1,3-dimethyl-3-(5,7-dimethylbenzothiazole-2-yl)urea,
1,1,3-trimethyl-3-(5,7-dimethylbenzothiazole-2-yl)urea,
2-chloro-4,6-diethylamino-1,3,5-triazine,
2-chloro-4-ethylamino-6-isopropylamino-1,3,5-triazine,
2-chloro-4,6-diisopropylamino-1,3,5-triazine,
2-methylmercapto-4-ethylamino-6-isopropylamino-1,3,5-triazine,
2-methylmercapto-4,6-diisopropylamino-1,3,5-triazine,
3-methoxycarbonylaminophenyl-N-(3'-methylphenyl)-carbamate, methyl N-(3,4-dichlorophenyl)carbamate,
isopropyl N-(3-chlorophenyl)carbamate,
S-(4-chlorobenzyl)-N,N-diethylthiol carbamate,
4'-nitro-2,4-dichloro-diphenyl ether,
4-nitro-2,4-6-trichloro-diphenyl ether,
2-methyl-4-chloro-phenoxyacetic acid,
2,4-dichloro-phenoxyacetic acid,
3-isopropyl-2,1,3-benzothiadiazine-4-one-2,2-dioxide,
and 1-phenyl-4-amino-5-chloro-pyridazine.

The concentrations of the active ingredients in the herbicidal composition of this invention vary according to type of formulation, and they are, for example, used in a range of 5 - 80 weight percent, preferably 10 - 60 weight percent, in wettable powder, 5 - 70 weight percent, preferably 20 - 60 weight percent, in emulsifiable concentrates, and 0.5 - 30 weight percent, preferably 1 - 10 weight percent in dust formulation.

Thus, a wettable powder or an emulsifiable concentrate produced thereto is diluted with water to a specified concentration and thereby, it is used as a liquid suspension or a liquid emulsion for treating soils or plant foliars. Further, a dust formulation is directly used for the soil treatment or the foliar treatment.

The non-limiting examples for the herbicidal composition are illustrated as follows:

Example 8

| Wettable Powder | Parts by weight |
| --- | --- |
| Compound 1 | 50 |
| Diatomaceous earth | 21 |
| Sodium alkylsulfate | 9 |
| Talc | 20 |

These are mixed homogeneously and reduced to fine particles. Consequently, wettable powder containing 50% of active ingredient is obtained. In practical use, it is diluted to a certain concentration with water and is sprayed as a suspension.

Example 9

| Emulsifiable Concentrate | Parts by weight |
| --- | --- |
| Compound 2 | 25 |
| Xylene | 50 |
| Dimethylformamide | 13 |
| Polyoxyethylene phenylether | 12 |
| These are mixed and dissolved. | |

These are mixed and dissolved.

Consequently, emulsifiable concentrate containing 25% of the active ingredient is obtained. In practical use, it is diluted to certain concentration with water and then is sprayed an emulsion.

Example 10

| Dust Formulation | Parts by weight |
| --- | --- |
| Compound 3 | 10 |
| Talc | 38 |
| Bentonite | 10 |
| Clay | 37 |
| Sodium alkylsulfate | 5 |

These are mixed homogeneously and reduced to fine particles. Fine particles are made into granules having the diameter in the range of 0.5 - 1.0 mm by granulator.

Consequently, dust formulation containing 10% of the active ingredient is obtained. In practical use it is directly applied.

The superior herbicidal effect of the novel compounds of this invention is clearly illustrated by the following test.

TEST 1

Pre-emergence treatment(soil treatment in paddy condition)

About 60 seeds of barnyard grass were planted in a pot having 60 square centimeters and covered slightly with soil. Water was poured into the pot until the surface of soil became wet.

10 ml of an aqueous emulsion prepared by diluting an emulsifiable concentrate with water to a specified concentration was sprayed on the pot. The pots were kept in a green house and water was added to the pots daily in order to keep the water level. Two weeks after spraying, the degrees of damage to the plant were observed and estimated by the values of 0 – 5 which have the following meanings:
0: no effect
1: partial plant slightly injured
2: plant slightly injured
3: plant moderately injured
4: plant severely injured
5: plant completely killed or no germination
The results were shown in Table 2.

Table 2

| Test Compound No. | Application rate (g/10 ares) | | | |
|---|---|---|---|---|
|  | 120 | 60 | 30 | 15 |
| 2 | 5 | 5 | 5 | 3 |
| 3 | 5 | 5 | 5 | 2 |
| 4 | 5 | 5 | 5 | 3 |
| 7 | 5 | 5 | 5 | 3 |
| 8 | 5 | 5 | 5 | 3 |
| 11 | 5 | 5 | 5 | 2 |
| 12 | 5 | 5 | 5 | 2 |
| 13 | 5 | 5 | 5 | 3 |
| 15 | 5 | 5 | 5 | 5 |
| 16 | 5 | 5 | 5 | 3 |
| 17 | 5 | 5 | 5 | 5 |
| 18 | 5 | 5 | 5 | 4 |
| 19 | 5 | 5 | 5 | 3 |
| 20 | 5 | 5 | 5 | 4 |
| 23 | 5 | 5 | 5 | 2 |
| 24 | 5 | 5 | 5 | 3 |
| 25 | 5 | 5 | 5 | 3 |
| Comparative compound* | 5 | 5 | 5 | 3 |

TEST 2

Pre-emergence treatment

Seeds of large crab-grass were planted in a pot having 100 square centimeters. 5ml of an aqueous emulsion prepared by diluting an emulsifiable concentrate with water to a specified concentration was sprayed on the surface of the soil before emergence. The pots were kept in a green house. 21 days after spraying, the degrees of damage to the test plants were observed and estimated by the value of 0 – 5 which have the same meanings as those of Test 1.

The results were shown in Table 3.

Table 3

| Test Compound No. | Application rate (g/10 ares) | | | |
|---|---|---|---|---|
|  | 250 | 125 | 62.5 | 31.3 |
| 3 | 5 | 5 | 5 | 3 |
| 4 | 5 | 5 | 5 | 3 |
| 8 | 5 | 5 | 5 | 4 |
| 12 | 5 | 5 | 5 | 3 |
| 19 | 5 | 5 | 5 | 4 |
| 20 | 5 | 5 | 5 | 4 |
| 24 | 5 | 5 | 5 | 3 |
| 25 | 5 | 5 | 5 | 3 |
| 27 | 5 | 5 | 5 | 3 |
| 28 | 5 | 5 | 5 | 3 |
| Comparative compound* | 5 | 5 | 5 | 4 |

TEST 3

Post-emergence treatment (foliar treatment)

Seeds of large crab-grass was planted in a pot having 100 square centimeters. When plants became 2 – 4 leaves stage, an aqueous emulsion prepared by diluting an emulsifiable concentrate with water to a specified concentration was sprayed on the foliar of the test plant at a rate of 100 liters per 10 are. The plants were kept in a green house.

21 days after spraying the degrees of damage to the test plant were observed and estimated by the value of 0 – 5 which have the same meaning as those of Test 1. The results wre shown in Table 4.

Table 4

| Test Compound No. | Application rate (g/10 are) | | | |
|---|---|---|---|---|
|  | 200 | 100 | 50 | 25 |
| 1 | 5 | 5 | 3 | 1 |
| 2 | 5 | 5 | 4 | 2 |
| 3 | 5 | 4 | 3 | 1 |
| 4 | 5 | 5 | 5 | 3 |
| 8 | 5 | 5 | 5 | 4 |
| 11 | 5 | 5 | 4 | 2 |
| 12 | 5 | 5 | 3 | 1 |
| 13 | 5 | 5 | 5 | 3 |
| 17 | 5 | 5 | 4 | 2 |
| 18 | 5 | 5 | 4 | 2 |
| 19 | 5 | 5 | 3 | 2 |
| 20 | 5 | 5 | 4 | 2 |
| 23 | 5 | 5 | 3 | 2 |
| 24 | 5 | 5 | 3 | 1 |
| 25 | 5 | 5 | 5 | 4 |
| 28 | 5 | 5 | 3 | 1 |
| Comparative compound | 5 | 5 | 3 | 1 |

TEST 4

Post-emergence treatment (foliar treatment in paddy condition)

About 50 seeds of barnyard grass were planted in a pot having 60 square centimeters and covered slightly with soil. Said pot was filled with water to about 3 cm above the surface of the soil when the plant was grown to first leaf-stage.

An aqueous emulsion prepared by diluting an emulsifiable concentrate with water to a specified concentration was sprayed on the pot. The pots were kept in a green house and water was added to the pot daily in order to keep the water level. Two weeks after spraying, the degrees of damage to the test plant was observed and estimated by the values of 0 – 5 which have the same meanings as those of Test 1.

The results were shown in Table 5.

Table 5

| Test Compound No. | Application rate (g/10 ares) | | | |
|---|---|---|---|---|
|  | 250 | 125 | 62.5 | 31.5 |
| 2 | 5 | 5 | 4 | 2 |
| 3 | 4 | 5 | 4 | 2 |
| 4 | 5 | 5 | 5 | 4 |
| 7 | 5 | 5 | 4 | 1 |
| 8 | 5 | 5 | 5 | 4 |
| 11 | 5 | 5 | 4 | 2 |
| 12 | 5 | 5 | 4 | 2 |
| 13 | 5 | 5 | 5 | 3 |
| 15 | 5 | 5 | 5 | 4 |
| 16 | 5 | 5 | 5 | 4 |
| 17 | 5 | 5 | 5 | 5 |
| 18 | 5 | 5 | 5 | 5 |
| 24 | 5 | 5 | 4 | 2 |

Table 5-continued

| Test Compound No. | Application rate (g/10 ares) | | | |
|---|---|---|---|---|
| | 250 | 125 | 62.5 | 31.5 |
| Comparative Compound* | 5 | 5 | 4 | 2 |

*Offenlegungsschrift 2352661 3-(1-N-ethoxyaminopropylidene)-6-ethyl-3,4-dihydro-2H-pyrane-2,4-dione

Figure 1:
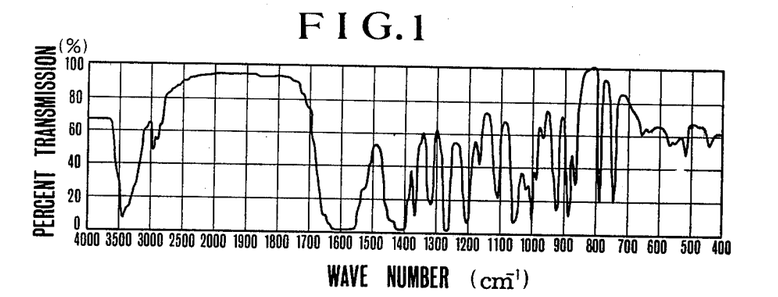
FIG. 1 is the infrared spectrum of Compound No. 11.
Figure 2:
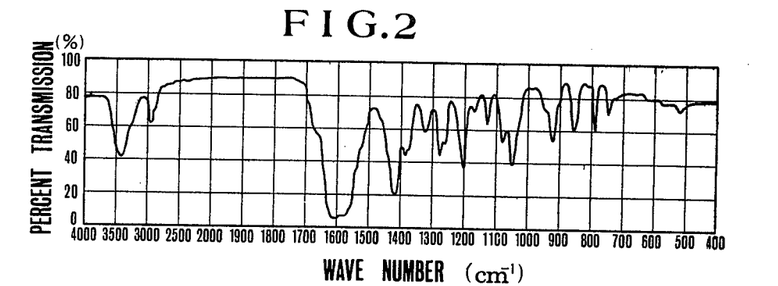
FIG. 2 is the infrared spectrum of Compound No. 12.
Figure 3:
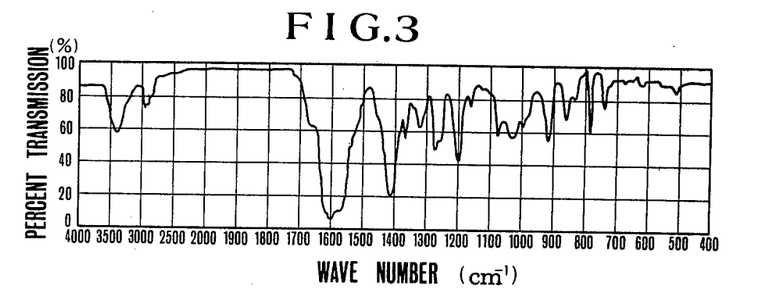
FIG. 3 is the infrared spectrum of Compound No. 13.
Figure 4:
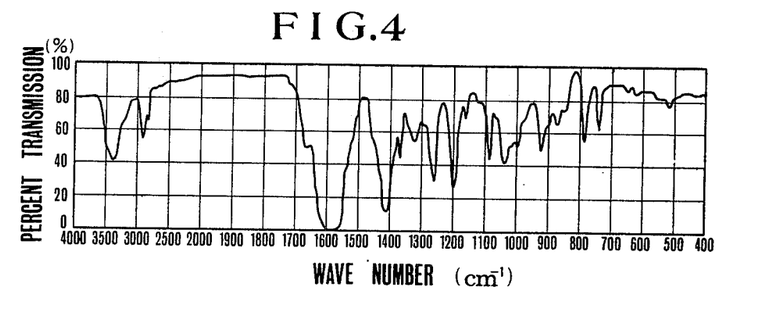
FIG. 4 is the infrared spectrum of Compound No. 14.

What is claimed is:

1. A compound of the general formula wherein
$R_1$ is alkyl of 1 to 3 carbon atom,
$R_2$ is selected from the group consisting of ethyl, allyl and propargyl,
$R_3$ is methyl when $R_4$ is methyl or ethyl,
or $R_3$ is hydrogen when $R_4$ is phenyl,
$R_4$ is selected from the group consisting of alkyl of 1 to 2 carbon atoms and phenyl, and
$R_3$ forms cyclo-alkylene of 4 to 5 carbon atoms by combining with $R_4$;
or sodium salt of the compound defined herein above.

2. A compound of the formula wherein
$R_1$ is selected from the group consisting of ethyl and propyl,
$R_2$ is selected from the group consisting of ethyl, allyl and propargyl,
$R_3$ and $R_4$ are methyl.

3. 2,2-dimethyl-5-[(1-allyloxyamino) propylidene]-1,3-dioxane-4,6-dione 4. 2,2-dimethyl-5-[(1-allyloxyamino)-n-butylidene]-1,3-dioxane-4,6-dione 5. A herbicidal composition containing an effective amount of a compound of claim 1.

6. A herbicidal composition containing an effective amount of a compound of claim 2.

7. A herbicidal composition containing an effective amount of a compound of claim 3.

8. A herbicidal composition containing an effective amount of a compound of claim 4.

9. A method for the control of weeds comprising applying a compound of claim 1 in an amount sufficient to excert herbicidal action to a locus to be protected.

10. A method for the control of weeds comprising applying a compound of claim 2 in an amount sufficient to excert herbicidal action to a locus to be protected.

11. A method for the control of weeds comprising applying a compound of claim 3 in an amount sufficient to excert herbicidal action to a locus to be protected.

12. A method for the control of weeds comprising applying a compound of claim 4 in an amount sufficient to excert herbicidal action to a locus to be protected.

* * * * *